(12) United States Patent
Allard et al.

(10) Patent No.: US 11,857,254 B2
(45) Date of Patent: Jan. 2, 2024

(54) METHOD AND SYSTEM FOR CHARACTERIZING THE VISUAL SYSTEM OF A SUBJECT

(71) Applicants: Essilor International, Charenton-le-pont (FR); Sorbonne Université, Paris (FR)

(72) Inventors: Rémy Allard, Champs sur Marne (FR); Daphné Silvestre, Paris (FR)

(73) Assignees: Essilor International, Charenton-le-pont (FR); Sorbonne Université, Paris (FR)

( * ) Notice: Subject to any disclaimer, the term of this patent is extended or adjusted under 35 U.S.C. 154(b) by 724 days.

(21) Appl. No.: 17/044,029

(22) PCT Filed: Mar. 28, 2019

(86) PCT No.: PCT/EP2019/057963
§ 371 (c)(1),
(2) Date: Sep. 30, 2020

(87) PCT Pub. No.: WO2019/185854
PCT Pub. Date: Oct. 3, 2019

(65) Prior Publication Data
US 2021/0093182 A1 Apr. 1, 2021

(30) Foreign Application Priority Data
Mar. 30, 2018 (EP) ..................... 18305379

(51) Int. Cl.
*A61B 3/00* (2006.01)
*G16H 50/30* (2018.01)
(Continued)

(52) U.S. Cl.
CPC .......... *A61B 3/0025* (2013.01); *A61B 3/0041* (2013.01); *A61B 3/022* (2013.01);
(Continued)

(58) Field of Classification Search
CPC ..... A61B 3/0025; A61B 3/0041; A61B 3/022; A61B 3/032; A61B 3/066; G16H 50/30; G16H 30/40
(Continued)

(56) References Cited

U.S. PATENT DOCUMENTS

2010/0007851 A1* 1/2010 Lu .................. A61B 3/028
                                                351/242
2017/0273553 A1   9/2017 Greivenkamp et al.

FOREIGN PATENT DOCUMENTS

EP   0228936       7/1987
EP   3222203 B1 *  3/2019  ............... A61B 3/00
(Continued)

OTHER PUBLICATIONS

Office Action issued in corresponding Chinese Application No. 2019800220784, dated Mar. 2, 2023.
(Continued)

*Primary Examiner* — James R Greece
(74) *Attorney, Agent, or Firm* — Norton Rose Fulbright US LLP

(57) ABSTRACT

The invention relates to a method for characterizing a visual system of a subject using measures of the sensitivity to contrast, the visual system comprising visual signal processing elements each having an impact on the sensitivity to contrast, wherein a visual test where visual patterns having different spatiotemporal frequencies and with varying luminance levels and with varying levels of visual degradation of the visual patterns are shown to a subject to measure the sensitivity to contrast of said subject, is performed, wherein a predetermined response model of a visual system is preestablished on the basis of a determination of the visual signal processing element that predominantly limits the sensitivity to contrast for each value of luminance and spatiotemporal frequency, said predetermined response
(Continued)

Figure 1:
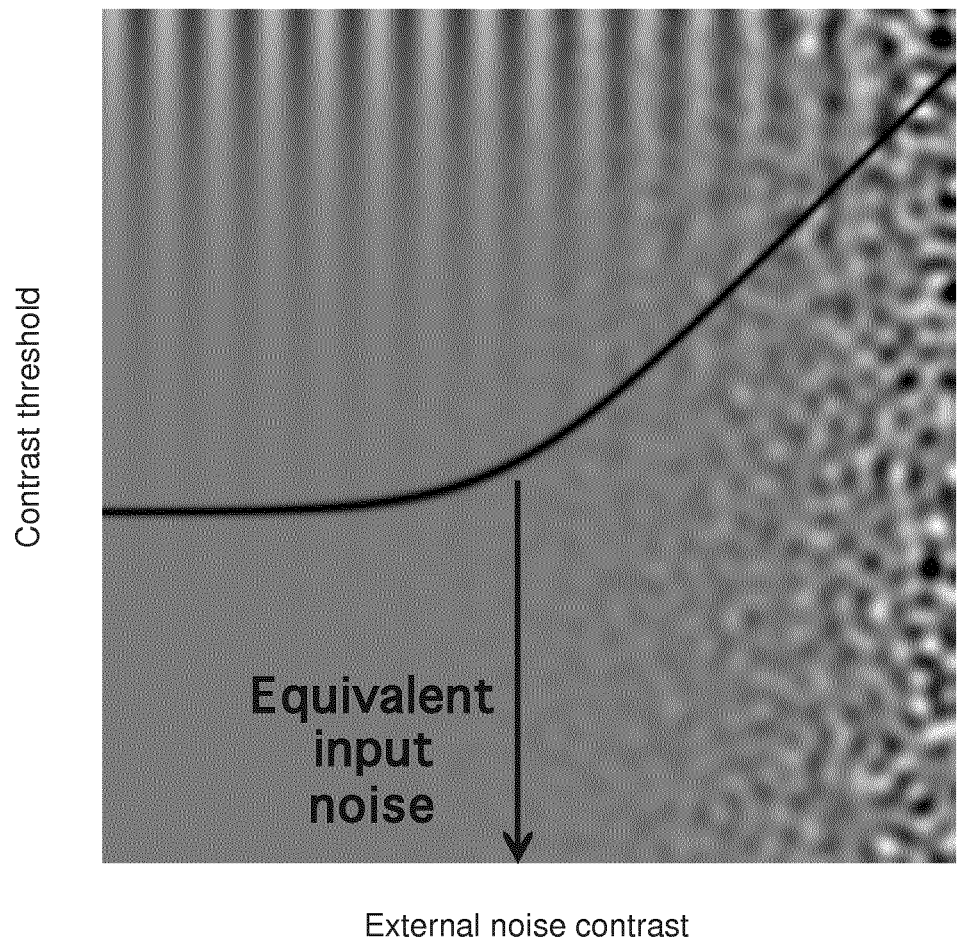

model relating the visual signal processing elements predominantly limiting the sensitivity to contrast to the luminances and to the spatiotemporal frequencies, wherein at least one of the visual signal processing elements is selected in order to be investigated, wherein at least one visual test is performed on the visual system of the subject, said visual test being optimized according to said at least one selected visual signal processing element, during the optimized visual test, the variations of the luminance levels and of spatiotemporal frequencies being limited within a range of luminance and a range of spatiotemporal frequency where the predetermined response model locates the visual signal processing element as predominant in limiting the sensitivity to contrast.

20 Claims, 3 Drawing Sheets

(51) Int. Cl.
   *G16H 30/40*    (2018.01)
   *A61B 3/02*     (2006.01)
   *A61B 3/032*    (2006.01)
   *A61B 3/06*     (2006.01)
(52) U.S. Cl.
   CPC .............. *A61B 3/032* (2013.01); *A61B 3/066* (2013.01); *G16H 30/40* (2018.01); *G16H 50/30* (2018.01)

(58) Field of Classification Search
   USPC ........................................ 351/200, 203, 246
   See application file for complete search history.

(56) References Cited

FOREIGN PATENT DOCUMENTS

| JP | H0997333 | 4/1997 | |
|----|----------|--------|---|
| JP | 2003169273 | 6/2003 | |
| JP | 2012037418 | 2/2012 | |
| WO | WO 2013/170091 | 11/2013 | |
| WO | WO-2013170091 A1 * | 11/2013 | .......... A61B 3/0025 |
| WO | WO 2015173605 | 11/2015 | |
| WO | WO 2017070445 | 4/2017 | |

OTHER PUBLICATIONS

International Search Report and the Written Opinion issued in corresponding International application No. PCT/EP2019/057963 dated Apr. 6, 2019.
Jarvis et al., "On the calculation of optical performance factors from vertebrate spatial contrast sensitivity", *Vision Research*, 47:2259-2271, 2007.
Pelli, D. "The quantum efficiency of vision.", Vision: Coding and Efficiency, C.Blakemore (ed), Cambridge University Press, New York, pp. 3-24, 1990.
Pelli et al., "Why use noise?" *J. Opt. Soc. Am. A Opt Image Sci Vis.*, 16(3):647-653, 1999.

* cited by examiner

METHOD AND SYSTEM FOR CHARACTERIZING THE VISUAL SYSTEM OF A SUBJECT

CROSS-REFERENCE TO RELATED APPLICATIONS

This application is a national phase application under 35 U.S.C. § 371 of International Application No. PCT/EP2019/057963 filed 28 Mar. 2019, which claims priority to European Patent Application No. 18305379.2 filed 30 Mar. 2018. The entire contents of each of the above-referenced disclosures is specifically incorporated by reference herein without disclaimer.

TECHNICAL FIELD OF THE INVENTION

The invention relates to a method for characterizing a visual system of a subject using measures of the sensitivity to contrast of the visual system of the subject. The invention is also related to a system specifically configured for operating the method of the invention.

BACKGROUND INFORMATION AND PRIOR ART

Studies have shown that the visual system of a subject could be considered as consisting of a set of elements that process the visual signal received in the eye of the subject, and that it could be mathematically and functionally considered as a set of operators performing operations on the received visual signal information. Each of the operations can be characterized by parameters and notably by an internal noise that is impacting the operation and more specifically, the capacity to receive, decode and understand the visual information. The more the internal noise, the less the subject is able to obtain meaningful information from the visual signal he/she has received. Practically, the set of elements can be limited to three elements: photoreceptors, proximal neuronal circuits and distal neuronal circuits. The impact of all the internal noises is generally referred as an "equivalent input noise" and the internal noises are, respectively, a photon noise in the photoreceptors, an early neural noise in the proximal neuronal circuits and a late neural noise in the distal neuronal circuits.

In other words, from the internal factors limiting the visibility of a visual stimulus, an important one is related to internal variations typically referred to as "internal noise". In the literature, the relative impact of internal noise on sensitivity can be estimated by measuring the amount of external noise, i.e. noise added to the display shown to the subject, that has the same impact as the internal noise (Pelli, 1990; Pelli & Farrell, 1999) and it is typically named "equivalent input noise". The sources of internal noise can be due to the stochastic absorption of photon by photoreceptors, named photon noise, or by neural noises. By measuring the equivalent input noise as a function of the luminance intensity, the impact of the three sources of internal noises (the photon noise, the early neural noise and the late neural noise) can be estimated. When late neural noise is the dominant limiting noise source, sensitivity is independent of luminance intensity. When early neural noise is the dominant limiting noise source, sensitivity is proportional to luminance intensity. When photon noise is the dominant limiting noise source, sensitivity is proportional to the square root of the luminance intensity. Additional information may be obtained in "The quantum efficiency of vision", in C. Blakemore (Ed.), Vision: Coding and efficiency, (pp. 3-24). Cambridge, UK: Cambridge University; and in Pelli, D. G., & Farell, B. (1999), "Why use noise?" Journal of the Optical Society of America. A, Optics, Image Science, and Vision, 16,647-653.

Moreover, it is necessary to perform visual tests on subjects for diagnostic purposes. This is also the case for prescription purposes, for example optical correction, in the case some adaptation of the prescription to the subject is wanted. The visual test of the sensitivity to contrast that can be used to evaluate the impact of the elements as a visual test is a very long and tedious process for a complete/full characterization of the visual system of the subject. Such a complete/whole visual test may take around two hours to perform because a plurality of parameters (notably luminance, frequency, external noise) needs to be scanned during the test.

SUMMARY OF THE INVENTION

It would be most useful to have a mean to reduce the time needed to test the visual system of a subject with a visual test of the sensitivity to contrast.

For that purpose, it is proposed to use information obtained from a preestablished/prior knowledge of the visual response of the visual system to focus/limit the visual test to the element or internal noise that should be assessed thanks to a limited/optimized visual test and, possibly, deduce/compute further information/results from such a limited/optimized visual test and that are normally obtained with a complete/whole visual test. The prior knowledge of the visual response of the visual system may be preestablished hypothetically or, better, on subjects by prior measures, in the form of a predetermined response model of the visual system. This predetermined response model may have been established preferably on a general or a specific population of subjects. That predetermined response model may be implemented in any useable form, for example tables, mathematical equation, graphical representation, a real-time computation from data.

Therefore, one object of the invention is to provide a method for characterizing a visual system of a subject using measures of the sensitivity to contrast of the visual system of the subject, the visual system comprising visual signal processing elements, each visual signal processing elements having an impact on the sensitivity to contrast of the visual system of the subject, wherein a visual test where visual patterns having different spatiotemporal frequencies and with varying luminance levels and with varying levels of visual degradation of the visual patterns are shown to a subject to measure the sensitivity to contrast of said subject, is performed, wherein a predetermined response model of a visual system is preestablished on the basis of a determination of the visual signal processing element that predominantly limits the sensitivity to contrast for each value of luminance and spatiotemporal frequency, said predetermined response model relating the visual signal processing elements predominantly limiting the sensitivity to contrast to the luminances and to the spatiotemporal frequencies, wherein at least one of the visual signal processing elements is selected in order to be investigated, wherein at least one visual test is performed on the visual system of the subject, said visual test being optimized according to said at least one selected visual signal processing element, during the optimized visual test the variations of the luminance levels and of spatiotemporal frequencies being limited within a range of luminance and a range of spatiotemporal frequency where the predetermined response model locates the visual signal processing element as predominant in limiting the sensitivity to contrast.

Following characteristics and means, that can be combined according to any technical possibility, are also considered for implementing the method of the invention:

- a response model of a visual system is established on the basis of a determination of the visual signal processing element that predominantly limits the sensitivity to contrast for each values of luminance and spatiotemporal frequencies, said determined response model relating the visual signal processing elements predominantly limiting the sensitivity to contrast to the luminances and to the spatiotemporal frequencies, said response model being a predetermined response model that has been preestablished on a general or specific population of subjects or being a personalized response model established on the subject that is having his/her visual system characterized,
- the visual signal processing elements are the elements pertaining to the chain of elements that is processing the visual signal, starting from the photoreceptors,
- the visual test is a static visual test where static visual patterns having different spatial frequencies and with varying luminance levels and with varying levels of visual degradation of the visual patterns are shown to the subject to produce the measures of the sensitivity to contrast, and/or a dynamic visual test where dynamic visual patterns having different temporal frequencies and with varying luminance levels and with varying levels of visual degradation of the visual patterns are shown to the subject to produce the measures of the sensitivity to contrast and thus of motion,
- the response model, being or not the predetermined one, is a static response model obtained with a static visual test and useable with static visual tests,
- the response model, being or not the predetermined one, is a dynamic response model obtained with a dynamic visual test and useable with dynamic visual tests,
- the response model, being or not the predetermined one, is a common response model useable with both static and dynamic visual tests,
- using the predetermined response model, it is possible to get the visual signal processing element predominantly limiting the sensitivity to contrast for a given luminance and a given spatiotemporal frequency, and, conversely, for a given visual signal processing element, it is possible to get the luminances and spatiotemporal frequencies where said the visual signal processing element is predominantly limiting the sensitivity to contrast,
- the predetermined response model gives the ranges of luminances and spatiotemporal frequencies where a given visual signal processing element is predominantly limiting the sensitivity to contrast,
- the predetermined response model gives the domains of location of each visual signal processing element that predominantly limits the sensitivity to contrast as a function of luminances and spatiotemporal frequencies,
- in the visual test, the sensitivity to contrast is assessed using static visual patterns,
- in the visual test, the sensitivity to contrast is assessed only using dynamic visual patterns,
- in the visual test, the sensitivity to contrast is assessed using separate static visual patterns and dynamic visual patterns,
- in the visual test, the sensitivity to contrast is assessed, using only one kind of visual patterns mixing or combining static and dynamic visual representations,
- preferably, in the visual test, each of the patterns has a spatial frequency value and a temporal frequency value, with none or one of the two that could be set to 0, the sensitivity to contrast being assessed using only one kind of visual patterns, for a static visual test the temporal frequency of the patterns being set to 0, for a dynamic visual test, the spatial frequency being preferably set to a value greater than 0, typically around 0.5 cpd, or less preferably set to 0,
- the visual patterns are contrasted lines, horizontal or vertical, symbols, letters, or any other type of pattern,
- the visual pattern has a spatial frequency and a temporal frequency values,
- the range of luminance and spatiotemporal frequency is further limited to a couple of luminance and frequency or a set of couples of luminances and frequencies used in the performed visual test,
- the response model, being or not the predetermined one, is a 2D response model,
- the predetermined response model is a 2D predetermined response model,
- the visual test can be a whole visual test in which whole ranges scans of luminance levels and frequencies are implemented for all visual processing elements or can be an optimized visual test in which the luminance levels and frequencies are limited within a range of luminance and a range of spatiotemporal frequency where the predetermined response model locates the visual signal processing element as predominant in limiting the sensitivity to contrast,
- in the predetermined response model, the visual signal processing elements predominantly limiting the sensitivity to contrast is quantified as a function of the level of limitation of the sensitivity to contrast in relation to the luminance and spatiotemporal frequency,
- in the response model, being or not the predetermined one, the visual signal processing elements predominantly limiting the sensitivity to contrast is quantified as a function of the level of limitation of the sensitivity to contrast in relation to the luminance and spatiotemporal frequency,
- the response model, being or not the predetermined one, in which the visual signal processing elements predominantly limiting the sensitivity to contrast is quantified, is a 3D response model,
- the predetermined response model in which the visual signal processing elements predominantly limiting the sensitivity to contrast is quantified, is a 3D predetermined response model,
- in the predetermined response model, the quantification is computed for each element from the parameters of at least one linear curve, notably a slope, corresponding to the element,
- the visual degradation of the visual pattern is obtained by applying an external noise to the visual pattern,
- the impact of each visual signal processing element on the sensitivity to contrast is quantified as an equivalent input noise value of the visual signal processing element,
- the predetermined response model relates the internal noise of the visual signal processing elements predominantly limiting the sensitivity to contrast to the luminances and to the spatiotemporal frequencies, the predetermined response model relates the equivalent input noise of the visual signal processing elements predominantly limiting the sensitivity to contrast to the luminances and to the spatiotemporal frequencies, the equivalent input noise is the external noise level at which the external and internal noises have the same impact on the sensitivity to contrast, three visual signal processing elements can be selected, each one being referenced by its internal noise, respectively, a photon noise, an early neural noise and a late neural noise, and during the visual test, the equivalent input noise of each visual signal processing element is evaluated by varying the external noise during contrast threshold assessments, in the contrast threshold assessment, the equivalent input noise is evaluated with reference to a determinable level of the external noise, said the equivalent input noise being evaluated due to the fact that during variations of the level of external noise, the later impacts or not the sensitivity to contrast as a function to its level, in the contrast threshold assessment, the equivalent input noise for a given luminance and a given spatial or temporal frequency is equal to the external noise when the later starts to sensibly decrease the sensitivity to contrast in case the external noise was increased during the test or, conversely, the equivalent input noise for a given luminance and a given spatial or temporal frequency is equal to the external noise level when the later sensibly stops to degrade the sensitivity to contrast in case the external noise was decreased during the test, the determination of the starting of decreasing of sensitivity to contrast or, conversely, the stop of the degradation is done with relative thresholds, the three visual signal processing elements are visual receptors, proximal neuronal circuits and distal neuronal circuits, the internal noises are a photon noise in the receptors, an early neural noise in the proximal neuronal circuits and a late neural noise in the distal neuronal circuits, the contrast threshold assessment is a total assessment in which, for a given luminance and a given frequency, the sensitivity to contrast of the subject is measured for a complete range of external noise levels during the variation of the external noise, the complete range of external noise levels is between a low or null/zero level of external noise for which the external noise has no impact on the sensitivity to contrast and a high level of external noise for which the external noise has an impact on the sensitivity to contrast by decreasing it, the contrast threshold assessment is a simplified assessment in which for a given luminance and a given spatiotemporal frequency the sensitivity to contrast are measured for only two levels of external noise, a low or null/zero level of external noise for which the external noise has a negligible impact on the sensitivity to contrast and a high level of external noise for which the external noise has a considerable impact on the sensitivity to contrast by decreasing it, giving two measures, wherein, a predetermined sensitivity model relating the sensitivity to contrast to the external noise is preestablished, and wherein the equivalent input noise, is computed by applying the said two measures to the predetermined sensitivity model, the external noise that has a negligible impact on the sensitivity to contrast is the one that has an impact that is not differentiable from the absence of external noise during the assessment, the external noise that has a negligible impact on the sensitivity to contrast is the one that has an impact level that is lower than a predefined threshold value, the contrast threshold assessment can be a total assessment in which a scan of external noise levels is implemented or can be a simplified assessment in which only one external noise level impacting the sensitivity to contrast is implemented or only two external noise levels are implemented, the high level of external noise for which the external noise has a considerable impact on the sensitivity to contrast is such that the subject is not anymore capable of detecting a contrast, the high level of external noise for which the external noise has a considerable impact on the sensitivity to contrast is the one that has an impact level that is greater than a predefined threshold value, the predetermined sensitivity model relating the sensitivity to contrast to the external noise is a predetermined static sensitivity model in case the visual test is a static visual test, the predetermined sensitivity model relating the sensitivity to contrast to the external noise is a predetermined dynamic sensitivity model in case the visual test is a dynamic visual test the predetermined sensitivity model relating the sensitivity to contrast to the external noise is a predetermined common sensitivity model useable for both static and dynamic visual tests, in the simplified assessment, the equivalent input noise, is computed by applying the said two measures to the predetermined sensitivity model to compute where the level of external noise sensibly starts to decrease the sensitivity to contrast or, conversely, sensibly stops to degrade the sensitivity to contrast, the equivalent input noise being then equal to the corresponding level of external noise, the predetermined sensitivity model relating the sensitivity to contrast to the external noise is preestablished from prior whole, as opposed to optimized, visual tests, the predetermined sensitivity model relating the sensitivity to contrast to the external noise is preestablished from prior whole, as opposed to optimized, visual tests on general or specific populations of subjects, the response model, being or not the predetermined one, is obtained from prior whole, as opposed to optimized, visual tests, the response model, being or not the predetermined one, is obtained from prior whole, as opposed to optimized, visual tests on general or specific populations of subjects or a subject, the predetermined sensitivity model linking the sensitivity to contrast as a function of the external noise is independent of the luminance and of the spatial or temporal frequency at which the test is done, the predetermined sensitivity model linking the sensitivity to contrast as a function of the external noise is also function of the luminance at which the visual test is done, the predetermined sensitivity model linking the sensitivity to contrast as a function of the external noise is also function of the spatial or temporal frequency at which the visual test is done, the predetermined sensitivity model linking the sensitivity to contrast as a function of the external noise is also function of both the luminance and of the spatial or temporal frequency at which the visual test is done, in the simplified assessment the two levels of external noise are a null/zero level of external noise for which the external noise has no impact on the sensitivity to contrast and a high level of external noise for which the external noise has an impact on the sensitivity to contrast by decreasing it, the results of the visual test or of a personalized response model constructed based on the results of the visual test are compared to the predetermined response model or to another response model, said another response model is a response model established from a general or specific population of subjects or on a reference subject, the specific population of subjects is selected from the general population of subjects accord to at least one characteristic from age, sex . . .

said another response model is a personalized response model established previously on the same subject as an historical reference, the personalized response model constructed based on the results of the visual test is obtained by adjustment/fitting of the predetermined response model to the results of the visual test, the results of the visual test are used to adjust the predetermined response model to the subject to produce a personalized response model, the predetermined response model and, in case of production of a personalized response model, the personalized response model, are presented on a graph representing the dominant sensitivity limiting visual signal processing element or its internal noise as a function of at least one parameter selected from at least: the luminance level, the spatial frequency, the temporal frequency, the eccentricity, the direction, the color, the light spectrum, the predetermined response model and, in case of production of a personalized response model, the personalized response model, are presented on a two or three dimensions graph representing the dominant sensitivity limiting visual signal processing element or its internal noise as a function of the luminance levels and of the spatiotemporal frequencies, multiple characterizations are done, each characterization being done for a specific color range or light spectrum, the characterizations are done with 2 colors/light spectrum and white, the characterizations are done with 3 colors/light spectrum and white, the characterizations are done with 3 colors, the characterization is done for all eccentricities of the vision, multiple characterizations are done, each characterization being done for a specific eccentricity of the vision, the specific eccentricities of the vision are related to specific anatomical area of the retina, a characteristic of a density filter intended to reduce the luminance intensity received by the visual system of the subject is calculated, the characteristic of the density filter being a value of luminous attenuation and being function of the results of optimized visual tests investigating at least two of the visual signal processing elements, one of them being the source of the late neural noise, the calculated value of luminous attenuation is a function of the relative distribution or ratio of the late neural noise and the photon noise, the calculated value of luminous attenuation is a function of the relative distribution or ratio of the late neural noise and the early neural noise, the subject is involved in an intended activity in which his/her visual system is used, possible activities requesting different visual sensitivity to contrast, the value of luminous attenuation being lower for activities requesting a higher visual sensitivity to contrast than for activities requesting a lower visual sensitivity to contrast, the value of luminous attenuation being calculated function of the intended activity and of the late neural noise obtained from the at least one optimized visual test done on the subject, the higher the late noise the higher the value of luminous attenuation, the calculated value of luminous attenuation is also selected according to a color range or light spectrum, the test being done for said color range or light spectrum, the calculated value of luminous attenuation is a predetermined value selected from a set of predetermined values, each predetermined value of the set being associated with one parameter in relation to an activity or to a requested level of sensitivity to contrast and wherein each predetermined value of the set is computed from the late neural noise or from the relative distribution of the late neural noise and photon noise as defined by the predetermined response model, the calculated value of luminous attenuation selected from a set of predetermined values is also selected according to a color range or light spectrum, the calculated value of luminous attenuation is also function of a characteristic of the subject selected from at least his/her age, the luminous attenuation of the density filter is chosen as:
  static and equal to the calculated value of luminous attenuation, or
  variable, the density filter being a variable density filter, in the case the luminous attenuation is variable, the highest value of luminous attenuation of the variable filter is the calculated value of luminous attenuation, in the case the luminous attenuation is variable, a sensor measuring the illumination reaching the subject is implemented and the luminous attenuation of the variable density filter is adjusted according to the measured illumination in order to maintain the vision of the subject at a determined level of performance, the density filter is neutral, the density filter is colored, the luminous attenuation of the density filter is binary and can flip between two values, a lowest value and a highest value, the luminous attenuation of the density filter is linear or stepwise between two values, a lowest value and a highest value, the lowest value is null/zero with no luminous attenuation or a negligible luminous attenuation, the highest value of the luminous attenuation of the density filter is the calculated value of luminous attenuation, a sensor measuring the size of the pupil of the subject is implemented and the luminous attenuation of the density filter is adjusted in order to keep sensibly constant the size of the pupil, in case the luminous attenuation of the density filter is variable, an input device useable by the subject allows him/her to enter and/or change the intended activity or the luminous attenuation, the luminous attenuation of the density filter is isotropic, the luminous attenuation of the density filter is homogenous, the luminous attenuation of the density filter is anisotropic, the calculated value of luminous attenuation is also function of a characteristic in relation to the subject, said characteristic being at least an intended activity of the subject, possible activities requesting different sensitivity to contrast by the subject, the calculated value of luminous attenuation is also function of a characteristic in relation to the subject, said characteristic being at least an intended activity of the subject, possible activities requesting different spatiotemporal frequencies, the characterization is done with a computerized system having a display that display visual patterns and the results of the visual tests are compared to warning thresholds and when a result overpass its related warning threshold then a warning is issued by the computerized system, the warning thresholds are defined with reference to a predetermined response model, said response model having been preestablished on a general population of subjects or a specific population of subjects or a reference subject, the issue of a warning means that there could be some disease, the display is a spectacle/google, the display is a computer screen, the warning thresholds are in relation to ratio of 2 of the photon noise, early neural noise and late neural noise, the warning thresholds are in relation to the relative levels of the photon noise, early neural noise and late neural noise, the warning thresholds are dependent of the direction of vision and/or color.

A further object of the invention is to provide a system for characterizing a visual system of a subject using measures of the sensitivity to contrast of the visual system of the subject specially configured to execute the method according to anyone of previous claims, wherein it is a computerized system having a display that display visual patterns and means to input results of visual tests, wherein it is configured to compare the results of visual tests to warning thresholds and to issue a warning when a result overpass its related warning threshold.

One major benefit of this approach is that the testing stage limits the space of exploration and more particularly the range of variations of luminance and of spatial or temporal frequency during the visual test. It is also possible to limit the range of variation to one or a few couple of luminance and spatial or temporal frequency values.

This solution provides other advantages and results as regards prescription and diagnostic because this possibility of limiting the space of exploration can help to focus the exploration on specific elements that are directly related to the prescription or diagnostic. For example, a disease may be related to a specific element of the visual system that can be response dominant in the test within a specific range of variations of luminance and of spatial or temporal frequency and if the test is limited to that range of luminance and of spatial or temporal frequency then the element is specifically assessed and the duration of the test much reduced.

DETAILED DESCRIPTION OF EXAMPLE(S)

Figure 2:
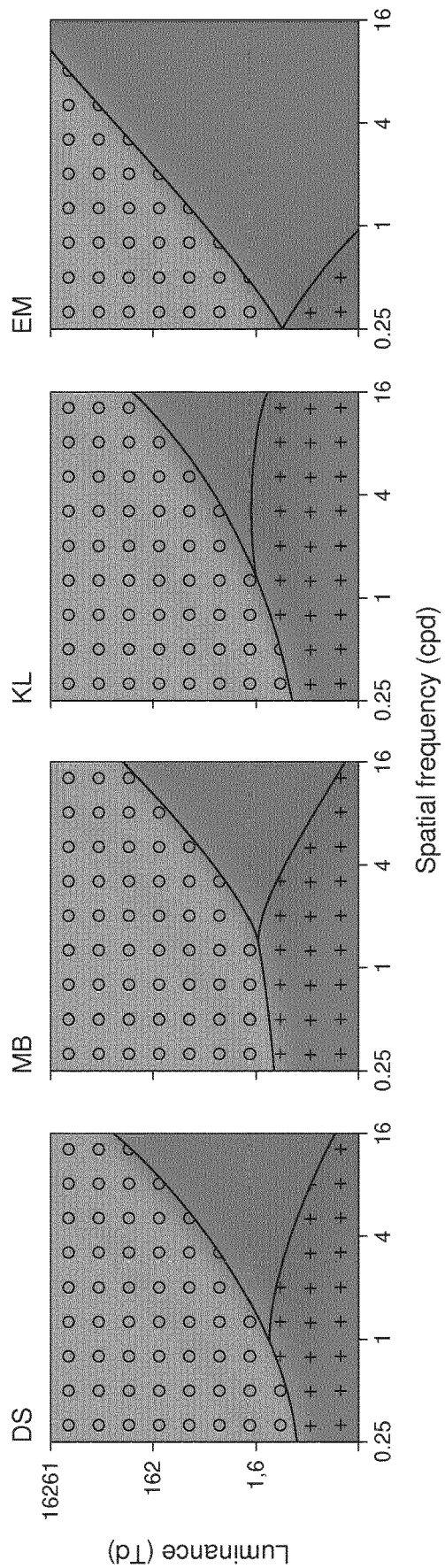
Figure 3:
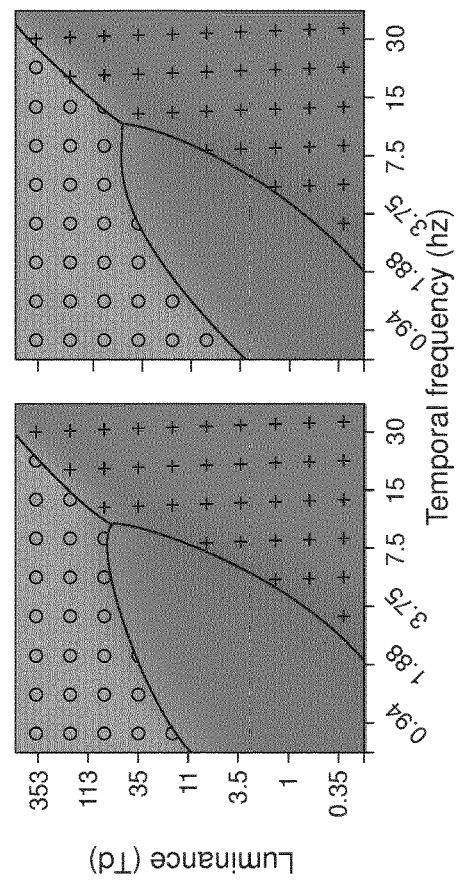
Figure 4:
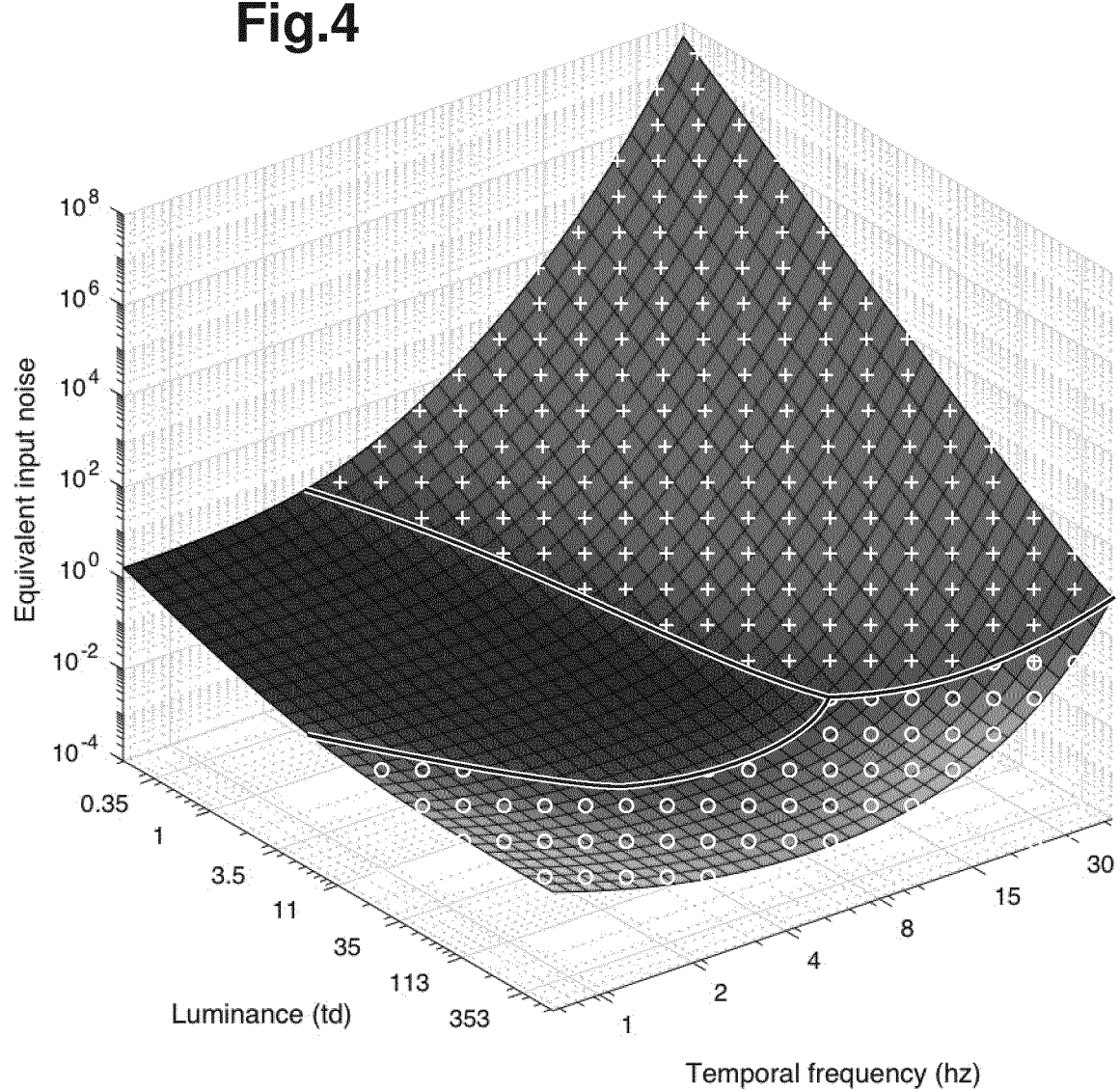
Figure 5:
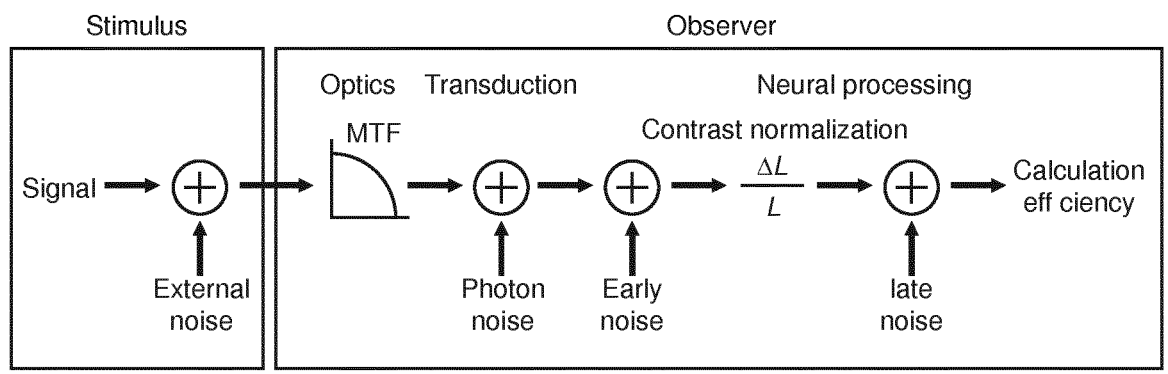

The invention will be better understood with the following description in relation to the following figures:

FIG. 1 represent the evolution curve of the contrast threshold as a function of external noise contrast for a given value of luminance and a given value of spatial or temporal frequency of a visual pattern, FIG. 2 represent the areas of dominant internal noise source as a function of the luminance intensity in Troland and of the spatial frequency of static visual patterns for four different subjects, the dominant internal noise being photon noise, early neural noise or late neural noise, the late neural noise area being represented with a pattern of "°", the early neural noise area with a pattern of "+" and the photon noise being plain, this two dimensions representation is obtained from a personalized response model of each subject, FIG. 3 represent the areas of dominant internal noise source as a function of luminance intensity in Troland and of the temporal frequency of dynamic visual patterns for two different subjects, this two-dimensions representation is obtained from a personalized response model of each subject, FIG. 4 is a three dimensions representation derived from FIG. 3 but obtained from a response model in which the impact of internal noise has been quantified, and FIG. 5 is a schematic representation of the operations of the visual system that takes into account the impact of the action of each element in the form of an internal noise associated to the element.

In order to characterize the visual system of a subject, a visual test for measuring the sensitivity to contrast of the visual system of the subject is used.

For obtaining a predetermined response model of a visual system that gives the element or the internal noise source predominantly limiting the sensitivity to contrast as a function of the luminance and of the spatial or temporal frequency of the visual signal provided by a visual pattern, measures of the impact of internal noise of the elements should be done and the above mentioned visual test can also be used for that purpose. This response model is the expression of the law of the elements of the visual system that relates the sensitivity to contrast to the luminance and to the frequency.

The response model is based on the symbolization of the visual system as schematized FIG. 5. The response model is here limited from the transduction by the photoreceptors with their photon noise to the neural processing that is, in this example, separated in two elements with their related internal noises: early neural noise and late neural noise. Other types of symbolization of the visual system may be possible.

More particularly, considering the three elements of the visual system, for measuring the levels of photon, early and late neural noises, the technical solution consists in measuring the impact of various sources of internal noises of the subject. This is possible by studying with a visual test, the evolutions of the sensitivity to contrast of the subject with the variations of luminance intensity and spatiotemporal frequency. Such a method is for example documented in the article "Internal noise sources limiting contrast sensitivity" (Silvestre, Arleo & Allard, 2018).

An example of a visual test that measures the sensitivity to contrast, the measures being static or dynamic, of the visual system of the subject and the means to obtain the internal noises are now described.

Said visual test can be a static visual test where static visual patterns having different spatial frequencies and with varying luminance levels and with varying levels of visual degradation of the visual patterns are shown to the subject to produce the measures of the sensitivity to contrast. It can also be a dynamic visual test where dynamic visual patterns having different temporal frequencies and with varying luminance levels and with varying levels of visual degradation of the visual patterns are shown to the subject to produce the measures of the sensitivity to contrast. The visual degradation is created by adding an external noise to the visual pattern. Note that in the dynamic visual test, the patterns can also have a specific frequency or different spatial frequencies.

Most usually and preferably, the visual tests are performed with visual patterns that each have a spatial and a temporal frequency value, and it is possible to set one of the two values to 0. For a static visual test, the temporal frequency is then set to 0. For a dynamic visual test, the spatial frequency is typically set around 0.5 cpd, but rarely set to 0.

Such a visual test is performed in multiple steps where the sensitivity to contrast of the subject is assessed by assessing his/her contrast threshold as a function of an external noise added to the visual pattern for a given luminance level and a given spatial or temporal frequency of the visual pattern and this is repeated over ranges of luminance levels and frequencies.

To measure the impact of an internal noise source, contrast threshold can be assessed as a function of external noise contrast. If the internal noise has more impact than the external noise, then the external noise will be negligible and have no impact on contrast threshold. On the other hand, if the external noise has more impact than the internal noise, then it will affect performance. More precisely, considering FIG. 1, the flat, left portion of the black curve shows that the external noise has no or a negligible impact on contrast threshold and, on the other hand, on the right portion of the black curve of FIG. 1, the rising contrast threshold shows that the external noise starts to have an impact and overpass the internal noise. Thus, at the breaking point between the two left and right portions of FIG. 1, at which the external noise starts to affect contrast threshold, the internal and external noises have the same impact. At that breaking point, the impact of the internal noise is the same as the impact of the external noise and is the equivalent input noise. Such an assessment of the contrast threshold is done for a given spatial and temporal frequency and for a given luminance level. One can thus understand why a complete/whole visual test for assessing the sensitivity to contrast of the visual system of the subject, for which many frequencies and many luminances should be assessed is a rather lengthy and cumbersome test.

It is important to note that the black curve of FIG. 1 can be segmented in two: a sensibly flat/constant value portion on the left and a sensibly constant slope portion on the right. Thanks to that, it is possible to compute such a curve for a subject with only at least two measurements: at low level or, better, no external noise for computing the left portion of the curve and at high external noise level, impacting and impairing the sensitivity, for computing the right portion knowing, from previous study on subjects, the parameters, notably slope, of the right portion estimated as a linear part. For that purpose, a model of the curve is preestablished in the form of a predetermined static or dynamic sensitivity model linking/relating the sensitivity to contrast as a function of the external noise and that was preestablished, preferably, on a general or specific population of subjects or a reference subject. In another embodiment, it is also possible to use a more general sensitivity model in which the equivalent input noise is defined as a function of spatial frequency, temporal frequency and luminance intensity.

Such sensitivity models may be implemented, for example, in one or more mathematical formulae, data tables, chart . . . or any other forms that could be stored and/or used by a computer for computations.

Other types of estimations than the linear one may be used, separately for each portion, or globally for the whole curve. Not only the curve can be computed from only two measures, but also the breaking point and thus the equivalent input noise that quantifies the impact of the internal noise.

This simplification of the contrast threshold assessment with only two measures, low or null external noise and high external noise, is implemented with a predetermined static or dynamic (according to the case) sensitivity model linking/relating the sensitivity to contrast as a function of the external noise. Applying the two results of the two measures to the predetermined static or dynamic sensitivity model allows the computation of the above-mentioned curve and (or directly) the equivalent input noise. The sensitivity model can be implemented to produce the curve or directly the equivalent input noise and thus the internal noise. The predetermined static or dynamic sensitivity model can be preestablished for all luminances and frequencies of multiple predetermined static or dynamic sensitivity models can be preestablished for specific ranges of luminances and frequencies.

A computer can thus be programmed to give directly the impact of the internal noise from the results that are the two assessed/measured contrast thresholds, of the two measures at low or null and high external noise level, for a given spatial or temporal frequency and for a given luminance level.

One can thus easily understand that the use of a simplified contrast threshold assessment with only two levels of external noise in two measurements, one of which being null in a possible implementation, can reduce the duration of the visual test and simplify it very efficiently as compared to a total contrast threshold assessment in which a complete scan/range of levels of the external noise is implemented/tested.

By making such contrast threshold assessments and collecting equivalent input noise values for various luminance levels and spatiotemporal frequencies, it is possible to associate an equivalent input noise value as predominantly pertaining to one of the three elements and thus to the photon noise, the early neural noise or the late neural noise.

Knowing to which element, receptors or early or late neural circuits, pertains the predominant internal noise, a law or model or a map can be calculated which determines the limiting noise source as a function of various parameters such as luminance intensity, spatial frequency and temporal frequency. Such maps are represented on FIGS. 2 and 3 for the spatial frequencies/static contrast sensitivity and for the temporal frequencies/dynamic contrast sensitivity/motion sensitivity respectively. Such a map is in fact a representation of the law of the visual system that relates the sensitivity to contrast to the luminance and to the frequency and that law can also be expressed as a response model.

On FIG. 2, four different subjects were tested for their contrast sensitivity and on FIG. 3, only two different subjects were tested for their contrast sensitivity.

Those maps of FIGS. 2, 3 give the dominant internal noise source as a function of luminance intensity and spatial frequency, in other words, the internal noise that has the most impact on sensitivity as a function of the luminance and of the frequency. Equivalently, the maps of FIGS. 2, 3 could instead give the element (the receptors or the early neural circuit or the late neural circuit) that has the most impact on sensitivity as a function of the luminance and of the frequency. It should be understood that this representation on a map is just an example of the possible representations. For example, a map could be made for the elements instead of the noise. Moreover, the related information contained in such a map, here represented in a graphical format, could be represented and stored in other forms and for example in one or more mathematical formulae, data tables, chart . . . or any other forms that could be stored and/or used by a computer for computations.

The maps of FIGS. 2 and 3 are two dimensions maps because the element or related internal noise of the response model used is not quantified. On FIG. 4, the map is a three dimensions map because the response model used has quantified the element or, currently, the impact of the internal noise (the equivalent input noise) of the element that predominantly impact/limit the sensitivity to contrast as a function of the luminance and frequency.

The previous explanations on the visual tests are given because the invention is also based on a prior knowledge of the internal noise sources that limit the contrast sensitivities and more particularly, the source of noise predominantly limiting the contrast sensitivity for given spatiotemporal frequencies and luminance levels. That prior knowledge is typically established from complete/whole visual tests on a general or specific population of subjects or a reference subject and with implementation of a map giving the dominant internal noise source as a function of luminance intensity and spatial frequency.

More generally, this prior knowledge can be implemented in the form of a predetermined response model of the visual system, said predetermined response model giving the visual signal processing element or the internal noise predominantly limiting the sensitivity to contrast as a function of the luminance and of the spatial or temporal frequency. This predetermined map or response model is preestablished on a general or a specific population of subjects or on a reference subject and can be stored in a computer and later used for simplifying and optimizing further visual tests, then referred as optimized visual tests, that are done on individual/specific subjects for diagnostic or prescription purposes.

Many deduced data can be obtained from such a predetermined map or response model giving the dominant internal noise. In addition, many further diagnostic or prescription actions may be oriented and optimized based on the predetermined map or response model giving the dominant internal noise.

In this context of optimization of further visual test, the response model is preferably obtained from tests on a general or specific population of subjects or on a reference subject.

In other cases, a response model can be computed for a specific subject and it could be used as a reference for future visual tests on that subject and/or also simplify/optimize those future visual tests, this is then a personalized response model. The personalized response model can be advantageously computed from an adjustment computation of the predetermined response model or another response model.

An example of the use of the predetermined map or response model in the case of prescription is now described.

Sunglasses are often used for comfort although they can impair visual perception when the environment is not sufficiently bright. For instance, lower illumination can reduce contrast sensitivity. At high luminance intensities, contrast sensitivities are independent of luminance intensity so it is possible to improve the subject's comfort by reducing luminance intensity without degrading visual perception. However, if the illumination is reduced too much, sensitivity will be affected.

The critical brightness at which sensitivity is affected depends on many environmental factors including spatiotemporal frequencies of the relevant visual information the subject will have to visualize in his/her activity, as well as various individual internal factors such as levels of internal noise.

The relevant visual information (e.g., spatial frequency, temporal frequency and eccentricity) depends on the subject's activity (e.g., reading, driving, practicing a sport) and can be included to determine the luminance intensity level at which the sensitivity of the subject to the relevant visual information will be affected. For instance, if the subject's activity requires the visibility of low spatiotemporal frequencies in a relatively bright environment, then high-density filters can be used without affecting the sensitivity of the relevant information. On the other hand, if the subject's activity requires the visibility of high spatiotemporal frequencies in a dimmer environment, then high-density filters will likely affect the sensitivity of the relevant information.

It can be noted that the critical luminance intensity at which late neural noise is the dominant internal noise source is likely to depend on other variables such as eccentricity and this can be taken into account when performing the visual tests: visual tests can be performed for different eccentricities or directions, or more generally, different retinal locations. Same for colors or light spectrum: visual tests can be performed for different colors.

It is then preferable to adapt the prescription of density filter in order to select the optimal density for specific visual functions and conditions which will increase the subject's comfort and minimize his visual sensitivity losses.

The prescription may thus concern density filters reducing luminance intensity and, in the context of the invention, this is done according to the subject's sensitivity and in an efficient way. Filter can be active and passive. This approach applies as well as for young, midlife and senior wearers.

It can be deduced from the predetermined map that for the conditions under which sensitivity is limited by late neural noise, contrast sensitivity is independent of luminance intensity. In these conditions, luminance intensity can be reduced with a density filter for example without affecting the sensitivity to the stimulus. It is then possible, for an adaptation to the subject, to identify, with an optimized visual test on the subject, the lowest luminance level at which the sensitivity is limited by late neural noise, i.e. at which sensitivity is independent of luminance intensity, to define the filter density that can be implemented without affecting sensitivity or, eventually, minimizing sensitivity losses.

That optimized visual test is using a limited range of luminance levels and of frequencies thanks to the predetermined map or response model that gives the ranges of luminance levels and frequencies were the visual test is assessing the relevant element or its internal noise. For a prescription of a density filter, the relevant internal noise to consider is the late neural noise but, for a better adaptation of the prescription, the relevant internal noises to consider are the late neural noise and the photon or early noise and more particularly the boundary between them. Therefore, for an adapted prescription of a density filter, a couple of luminance value and frequency value for the late neural noise can be used or, better, two couples for respectively the late neural noise and the photon or early noise.

In addition, the ranges for the visual test can also be adapted to other parameters such as the subject needs. For example, for the adaptation, the range for the frequency used in the optimized visual test can also be selected according to the type of information, low or high frequency, the subject will have to visually observe, and the predetermined map or response model will give the related luminance levels for the visual test and this is still a limited range compared to a whole visual test.

The invention can be useful to different segments of population having different levels of internal noise and the predetermined map or response model can be preestablished for a specific segment of population. For instance, the luminance intensity at which it affects contrast sensitivity is increased with aging and thus it is preferable to do optimized visual tests on the older subjects with ranges or values of luminance and frequencies limited according to the predetermined map or response model preestablished on a population of older subjects. If the density filter is not adapted to the subject, it can have a greater impact for older subjects than for younger.

The critical luminance intensity at which sensitivity is optimal, i.e. when sensitivity is limited by late neural noise, is higher at high spatiotemporal frequencies. Consequently, if high spatiotemporal frequencies are relevant to the task of the subject, then the luminance intensity cannot be reduced as much. Thus, the activity of the subject with his sensitivity determines the critical level of brightness under which it is preferable that luminance intensity does not drop. For instance, high spatial frequencies are relevant for reading and high temporal frequencies are relevant for playing a highly dynamical sport such as tennis. Thus, in these conditions, the ambient luminance intensity would preferably need to be relatively high so that the limiting internal noise source at all spatiotemporal frequencies is late neural noise. For example, with a luminance intensity above about 350 Td, the limiting noise source is generally late neural noise which would largely preserve the sensitivity to high spatiotemporal frequencies. But for activities that do not necessitate the processing of high spatiotemporal frequencies, e.g. relaxing on the beach, rock climbing or hiking, then luminance intensity could be further reduced to improve the subject's comfort. For instance, a retinal illumination around 35 Td would have little impact on sensitivity to low spatial and temporal frequencies.

Note that the critical smallest luminance intensity at which sensitivity to the relevant frequencies is limited by late neural noise can vary greatly with subject ages and, again, an adaptation with an optimized visual test on the subject is most preferable.

Given the selected optimal retinal illumination, an active filter can be created to keep the brightness above the critical brightness. The retinal illumination depends on the ambient illumination, the pupil size and the density filter. The pupil size needs to be known around the targeted retinal illumination, e.g. 35 Td in the last example. This can be empirically measured or estimated based on current models. Given the known pupil diameter around the targeted retinal illumination, e.g. 3 mm, then the targeted luminance intensity can be computed. Indeed, the retinal illumination in Td is equal to the brightness in $cd/m^2$ multiplied by the pupil area in $mm^2$. Thus, if the target retinal illumination is 350 Td at which the pupil is 3 mm, then the targeted luminance intensity is $350/(pi*(3/2)^2)=50$ $cd/m^2$. Consequently, if the luminance intensity of the environment is 500 $cd/m^2$, then the density filter should block about 90% of the light for the retinal illumination to be 350 Td. This method would ideally be implemented in an active filter basing the filter density on the ambient light. For passive filters, roughly estimating the standard brightness level during the activity of the subject would be required to calculate the density of the filter.

The visual test can also take into account the eccentricity and the direction of vision and the internal noises can be assessed for different eccentricities and directions. In addition, predetermined maps or response models can be computed for different eccentricities and directions. It is then possible to draw a geographical map of the eye giving for each cornea regions the dominant internal noise for a given luminance and frequency or any other representation of those parameters: region/angle and luminance and frequency and dominant internal noise/related element.

Thus, the noise maps indicating the limiting noise source as a function of spatial frequency and/or temporal frequency and luminance intensity can also be measured at different eccentricities or directions. Those maps or even the corresponding models, may have any number of dimensions, 2D, 3D . . . and reference axis, for examples as a function of spatial frequency and temporal frequency and luminance intensity. Other dimensions may be added of substituted such as the eccentricity and the directions, e.g. as a function of eccentricity and luminance intensity. More generally, the noise maps may indicate the limiting noise source as a function of varies variable, e.g., luminance intensity, spatial frequency, temporal frequency, eccentricity, directions, chromaticity . . . same for their corresponding models.

Because the cone density drops considerably with eccentricity, the level of photon noise will rise with eccentricity, so the limiting noise source will likely change with eccentricity. Consequently, the critical brightness level, i.e. the lowest luminance intensity at which late neural noise is the dominating internal noise source, will change with eccentricity and direction.

As an example, if the critical luminance intensity at which performance to the relevant frequencies is limited by late neural noise is 350 Td at the fovea and 100 Td at 50 degrees of eccentricity, then the density of the filter could block 3.5 times more light at 50 degrees of eccentricity. Thus, the density of the filter can also vary with eccentricity and direction.

To reduce retinal illuminance, it is possible to use passive or active filters that take into account the subject's sensitivity to retinal illuminance, i.e. the brightness at which sensitivity is affected, and the visual information that is relevant to the subject: static versus dynamic information, low versus high spatiotemporal frequencies.

The density filter may be implemented in an active spectacle that has, for example, electrochromic lenses allowing a variation of the light transmission and also having a luminance sensor. The level of light transmission is preferably controlled by the luminance sensor in order that the luminous flux received by the subject, in specific conditions, is equal or above the minimum luminance level giving an optimal contrast.

The prescription thus aims at characterizing the subject's sensitivity for a given activity in a given environment in order to define a density filter that will minimize the impact on the sensitivity of visual information relevant to the subject. The advantages of using information gained from a predetermined map or response model are that limited/optimized visual tests may be used to:

Prescribe a density filter personalized to the subject's sensitivity. This technic optimizes visual perception for a given subject.

Prescribe a density filter adapted/personalized to the subject's needs or activities, reading, navigation, driving, sports. The density of the filter can also be adjusted to optimize vision according to the subject's needs in order to optimize vision for specific tasks, e.g. low versus high spatiotemporal frequencies, central versus peripheral vision, low versus high luminance intensity.

An example of the use of the predetermined map or response model in the case of diagnostic is now described.

The diagnostic may concern the search for one or more potential visual diseases or impairments for a given subject or the evaluation of a known disease or impairment in a subject. In both cases, the visual test on the subject is limited/optimized because thanks to knowledge gained form the distribution of the dominant internal noise from the predetermined map or response model, and thus the dominant element affecting sensitivity, the search and evaluation are focused with visual tests that are done on a limited range of luminance or/and frequency or, even, on only one or a few couples of luminance and frequency values.

The visual receptors of the eye are rods and cones and they have different functions and repartitions in the cornea.

It is possible to estimate the cone absorption rate.

The photon noise measurement is caused by the stochastic absorption of photon by photoreceptors. Thus, the measurement of photon noise can be an indicator of the level of photon absorption rate, which depends on photoreceptor density and absorption efficiency. By measuring photon noise using different wavelengths, it is possible to measure the absorption rate of the different photoreceptor types, the three types cones and the rods. Incidentally, this information can be used to determine the chromaticity of the filter in order to minimize its impact on sensitivity in the case of a prescription.

The photoreceptor density can also be estimated as a function of eccentricity and direction, for lower and/or upper visual fields. For instance, it is well known that cone density drops with eccentricity and thus the photon noise varies with retinal location. Incidentally, this can be an indicator of adjusting the filtering density as a function of retinal location, e.g. different filter density gradient for lower and upper visual fields, in the case of a prescription.

More generally, because measuring photon noise reflects the absorption rate, it is an indicator of a pathological condition. For instance, age-related macular degeneration affects photoreceptors: higher photon noise at the fovea could indicate the beginning of this disease. Furthermore, some other pathological conditions could rather affect cone in the periphery and be related to higher photon noise in the periphery. The visual test that is implemented to check this/those conditions is optimized with a limited range of luminance levels and frequencies because a specific element is assessed, in this instance the photoreceptors and their internal noise that is the photon noise. From the predetermined map or response model one deduces that the photoreceptors can be assessed within a defined limited range of luminance levels and frequencies with the optimized visual test.

It is then possible to detect reduced photoreceptor density or efficiency with an optimized test requiring less time and being less cumbersome.

Again, the level of photon noise is an indirect measure of the number of photons being absorbed by photoreceptors. If the density of photoreceptors drops or if the photoreceptors become less efficient at absorbing photons, then the measured photon noise will increase. For instance, it has been found that older subjects, ~70 years, had about four times more photon noise than young subjects, ~25 years, suggesting that their photoreceptors absorbed about four times less photons. The density of photoreceptors and their efficiency can be assessed with an optimized visual test for measuring the photon noise using only high wavelengths, i.e. red stimulus, and an artificial pupil, the effect of the yellowing of the lens of the eye and myosis being thus neutralized.

In these conditions, it has been found that older subjects absorbed about four times less photons than younger ones, suggesting that older subject have less photoreceptors or their photoreceptors are less efficient. Consequently, the measure of photon noise can be useful to detect physiological changes at the photoreceptor level, e.g. healthy aging, and thereby detect developing pathologies, e.g. ARMD, which affects photoreceptors in central vision, or macular edema, which affects also affects photoreceptors in central vision as well as light transmission, or other diseases affecting the peripheral retina. In this context, a predetermined map or response model can also serve as a reference to make comparisons with the measured photon noise from the optimized visual test.

Indeed, a pathology that affects photoreceptors will affect the photon absorption rate and thereby the level of photon noise. Age-related macular degeneration, for instance, affects primarily photoreceptors in central vision, whereas retinitis pigmentosa rather affects photoreceptors in the periphery. By measuring the photon noise in central and peripheral vision, and comparing these levels relative to a standard baseline of a healthy population could result in an indicator of a potential disease. A patient having more photon noise in central vision than the baseline would suggest a problem with photoreceptor in central vision, e.g. ARMD. Conversely, a patient with abnormally high photon noise only in the periphery could be an indicator of a retinitis pigmentosa.

To efficiently assess the level of photon noise at fixation, contrast sensitivity needs to be measured, preferably using the simplified contrast threshold assessment with and without external noise, in conditions in which photon noise is known to be the main internal noise source, e.g. optimized visual test with only one couple of temporal frequency value, 2 Hz, and luminance intensity, 3 Td tested. To measure photon noise peripherally, e.g. 50 degrees of eccentricity, a similar approach can be used, but with the subject fixating at a fixation point away from the stimulus to detect.

Other elements of the visual system than the photoreceptors can be explored and, in particular, post-receptor retinal diseases.

Some diseases can affect retinal processing other than at the photoreceptor level, e.g. glaucoma. Such diseases are expected to affect early neural noise. Consequently, measuring a level of early neural noise for the proximal neuronal circuits greater than a standard healthy baseline can be an indicator of some retinal diseases.

To efficiently measure the level of early neural noise, contrast sensitivity needs to be measured, preferably using the simplified contrast threshold assessment with and without external noise, in conditions in which early neural noise is known to be the main internal noise source, e.g. optimized visual test with only one couple of temporal frequency value, 15 Hz, and luminance intensity, 100 Td, tested.

Still other elements of the visual system can be explored and for example to detect neurological disorders. In this instance, late neural noise could be an indicator of some diseases affecting neural processing, e.g. dementia, autism, schizophrenia, or some psychoactive drugs, e.g., alcohol, cannabis, cocaine, affecting neural processing due to intoxication or long-lasting alterations in brain function. Consequently, measuring higher than normal late neural noise of the distal neuronal circuits could be clinically used to seek for potential neurological disorder. In that instance, an optimized visual test focusing on the late neural noise can be implemented in the same manner as the previous ones for the other elements of the visual system.

As we have already seen, simplified contrast threshold assessment for measuring the level of internal noise for a given spatiotemporal frequency and a given luminance level requires only two measurements: contrast threshold in the absence of noise and in high noise to estimate the flat/constant and the rising asymptote parts of the curve and then compute the equivalent input noise thanks to the predetermined sensitivity model modeling the curve. This simplified assessment of contrast threshold allows on its own a substantial gain of time. Using this simplified contrast threshold assessment for measuring the impact of internal noise over a complete range of spatiotemporal frequency and luminance intensity in the whole visual test can thus allow a first reduction of the time it takes. But, with the invention, it is possible to gain much more time with a limitation of the ranges or of the couple(s) of frequencies and luminances that is/are tested thanks to the optimized visual test. For that purpose, a predetermined response model of a visual system that was made at a prior time is used. The element or internal noise that should be assessed is selected. This element or its internal noise is chosen essentially according to the goal of the characterization: the element concerned by the prescription or the diagnostic. The limited/optimized visual test is done with a limited range of variation of frequencies and luminance given by the predetermined response model for that element or internal noise or even limited to one or a few couples of frequency and luminance values.

Such a method can be implemented in an apparatus having computation means under the control of a program. The apparatus required to estimate the levels of internal noise is an apparatus enabling to measure contrast sensitivity under various parameters including luminance intensity, spatiotemporal frequency, eccentricity, color range and levels of external noise. To measure contrast sensitivity, such an apparatus would present some stimuli to the subject in the form of visual patterns, e.g. Gabor patch at a given spatiotemporal frequency, eccentricity and luminosity, who would need to make a judgment, e.g. Gabor patch vertically or horizontally oriented.

In order to manipulate the frequencies of the patterns, a display may be used with the apparatus, e.g. a computer screen. That display may be a static or a dynamic display. Furthermore, the luminance intensity needs to be quantified in retinal illumination, e.g. Trolands, which depends on the display luminance intensity and the pupil size. Ideally, the apparatus could automatically measure the pupil size to efficiently control the retinal illumination. Alternatively, an artificial pupil with a known fixed diameter, e.g. 2 mm, smaller than the subject's pupil can be put in front of the subject's pupil. Another possibility is that the pupil size is manually measured or automatically measured and the information is used to calculate the retinal illumination. The computer screen may be an active spectacle capable of displaying visual patterns and added variable noise.

The invention claimed is:

1. A method for characterizing a visual system of a subject using measures of the sensitivity to contrast of the visual system of the subject, the visual system comprising visual signal processing elements, each visual signal processing elements having an impact on the sensitivity to contrast of the visual system of the subject,
    wherein a visual test where visual patterns having different spatiotemporal frequencies and with varying luminance levels and with varying levels of visual degradation of the visual patterns are shown to a subject to measure the sensitivity to contrast of said subject, is performed;
    wherein a predetermined response model of a visual system is preestablished on the basis of a determination of the visual signal processing element that predominantly limits the sensitivity to contrast for each value of luminance and spatiotemporal frequency, said predetermined response model relating the visual signal processing elements predominantly limiting the sensitivity to contrast to the luminances and to the spatiotemporal frequencies;
    wherein at least one of the visual signal processing elements is selected in order to be investigated; and
    wherein at least one visual test is performed on the visual system of the subject, said visual test being optimized according to said at least one selected visual signal processing element, during the optimized visual test the variations of the luminance levels and of spatiotemporal frequencies being limited within a range of luminance and a range of spatiotemporal frequency where the predetermined response model locates the visual signal processing element as predominant in limiting the sensitivity to contrast.

2. The method according to claim 1, wherein the range of luminance and spatiotemporal frequency is further limited to a couple of luminance and frequency or a set of couples of luminances and frequencies used in the performed visual test.

3. The method according to claim 1, wherein the visual degradation of the visual pattern is obtained by applying an external noise to the visual pattern;
    wherein the impact of each visual signal processing element on the sensitivity to contrast is quantified as an equivalent input noise value of the visual signal processing element; and
    wherein the predetermined response model relates the equivalent input noise of the visual signal processing elements predominantly limiting the sensitivity to contrast to the luminances and to the spatiotemporal frequencies.

4. The method according to claim 3, wherein three visual signal processing elements can be selected, each one being referenced by its internal noise, respectively, a photon noise, an early neural noise and a late neural noise; and
    wherein during the visual test, the equivalent input noise of each visual signal processing element is evaluated by varying the external noise during contrast threshold assessments.

5. The method according to claim 4, wherein the contrast threshold assessment is a total assessment in which, for a given luminance and a given frequency, the sensitivity to contrast of the subject is measured for a complete range of external noise levels during the variation of the external noise.

6. The method according to claim 5, wherein the results of the visual test or of a personalized response model constructed based on the results of the visual test are compared to the predetermined response model or to another response model.

7. The method according to claim 5, wherein the results of the visual test are used to adjust the predetermined response model to the subject to produce a personalized response model.

8. The method according to claim 5, wherein the predetermined response model and, in case of production of a personalized response model, the personalized response model, are presented on a graph representing the dominant sensitivity limiting visual signal processing element or its internal noise as a function of at least one parameter selected from at least: the luminance level, the spatial frequency, the temporal frequency, the eccentricity, the direction, the color, the light spectrum.

9. The method according to claim 4, wherein the contrast threshold assessment is a simplified assessment in which for a given luminance and a given spatiotemporal frequency the sensitivity to contrast are measured for only two levels of external noise, a low or null/zero level of external noise for which the external noise has a negligible impact on the sensitivity to contrast and a high level of external noise for which the external noise has a considerable impact on the sensitivity to contrast by decreasing it, giving two measures, wherein, a predetermined sensitivity model relating the sensitivity to contrast to the external noise is preestablished, and wherein the equivalent input noise, is computed by applying the said two measures to the predetermined sensitivity model.

10. The method according to claim 9, wherein the results of the visual test or of a personalized response model constructed based on the results of the visual test are compared to the predetermined response model or to another response model.

11. The method according to claim 9, wherein the results of the visual test are used to adjust the predetermined response model to the subject to produce a personalized response model.

12. The method according to claim 4, wherein the predetermined response model and, in case of production of a personalized response model, the personalized response model, are presented on a graph representing the dominant sensitivity limiting visual signal processing element or its internal noise as a function of at least one parameter selected from at least: the luminance level, the spatial frequency, the temporal frequency, the eccentricity, the direction, the color, the light spectrum.

13. The method according to claim 3, wherein a characteristic of a density filter intended to reduce the luminance intensity received by the visual system of the subject is calculated, the characteristic of the density filter being a value of luminous attenuation and being function of the results of optimized visual tests investigating at least two of the visual signal processing elements, one of them being the source of the late neural noise.

14. The method according to claim 13, wherein the luminous attenuation of the density filter is chosen as:
   static and equal to the calculated value of luminous attenuation; or variable, the density filter being a variable density filter.

15. The method according to claim 14, wherein the calculated value of luminous attenuation is also function of a characteristic in relation to the subject, said characteristic being at least an intended activity of the subject, possible activities requesting different sensitivity to contrast by the subject.

16. The method according to claim 12, wherein the calculated value of luminous attenuation is also function of a characteristic in relation to the subject, said characteristic being at least an intended activity of the subject, possible activities requesting different sensitivity to contrast by the subject.

17. The method according to claim 1, wherein multiple characterizations are done, each characterization being done for a specific color range or light spectrum.

18. The method according to claim 1, wherein multiple characterizations are done, each characterization being done for a specific eccentricity of the vision.

19. The method according to claim 1, wherein the characterization is done with a computerized system having a display that displays visual patterns and wherein the results of the visual tests are compared to warning thresholds and when a result overpass its related warning threshold then a warning is issued by the computerized system.

20. A system for characterizing a visual system of a subject using measures of the sensitivity to contrast of the visual system of the subject specially configured to execute the method according to claim 1, wherein it is a computerized system having a display that displays visual patterns and means to input results of visual tests, wherein it is configured to compare the results of visual tests to warning thresholds and to issue a warning when a result overpass its related warning threshold.

* * * * *